United States Patent [19]
Arizono et al.

[11] Patent Number: 4,525,348

[45] Date of Patent: Jun. 25, 1985

[54] PRANOPROFEN GELLED OINTMENT

[75] Inventors: Kenzo Arizono; Michio Terasawa; Michiharu Nobutoki, all of Oita, Japan

[73] Assignee: Yoshitomi Pharmaceutical Industries, Ltd., Japan

[21] Appl. No.: 562,570

[22] Filed: Dec. 19, 1983

[51] Int. Cl.³ ............................................. A61K 31/78
[52] U.S. Cl. ...................................................... 424/81
[58] Field of Search .......................................... 424/81

[56] References Cited

U.S. PATENT DOCUMENTS 3,931,205  1/1976  Nakanishi et al. .................. 424/263
4,309,414  1/1982  Inagi et al. ............................ 424/81

FOREIGN PATENT DOCUMENTS 2023000  12/1979  United Kingdom .

Primary Examiner—Stanley J. Friedman
Attorney, Agent, or Firm—Sughrue, Mion, Zinn, Macpeak and Seas

[57] ABSTRACT

An antiinflammatory and analgesic gelled ointment contains pranoprofen, at least one member selected from the group consisting of lower aliphatic alcohol, polyethylene glycol, methyl ethyl ketone and acetone, a gelling agent selected from the group consisting of carboxyvinyl polymer, hydroxyethyl cellulose, alginic acid and carboxymethyl cellulose, a water-soluble basic substance selected from the group consisting of ammonia, sodium hydroxide, potassium hydroxide, triethanolamine, diethanolamine, diisopropanolamine, triisopropanolamine and triethylamine, and water.

6 Claims, No Drawings

PRANOPROFEN GELLED OINTMENT

This invention relates to an antiinflammatory and analgesic gelled ointment containing pranoprofen as an active ingredient.

Pranoprofen is a potent antiinflammatory, analgesic and antipyretic agent represented by the formula:

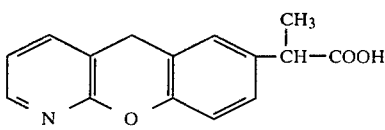

and described, for example, in U.S. Pat. No. 3,931,205.

Pranoprofen is now sold by the present applicant in Japan in the form of capsules as antiinflammatory and analgesic agent for the treatment of chronic rheumatic arthritis, as analgesic and antipyretic agent for the treatment of acute upper air-way inflammation, and as antiinflammatory and analgesic agent for the treatment after tooth extraction.

The oral administration of pranoprofen may cause, though very rarely, adverse effects such as gastroenteric disorders as compared with indomethacin or other nonsteroid antiinflammatory and analgesic agents.

In the treatment of local diseases such as arthritis, myalgia or pain after trauma, the local route is more advantageous than the systemic route in effectiveness and in avoidance of unknown or unexpected adverse effects.

From these points of view, the development of pranoprofen ointments has been strongly desired.

The U.S. Pat. No. 3,931,205 mentioned above describes that the pharmaceutical composition containing pranoprofen can take the form of cream, ointment or jelly and that the choice of carrier is determined by the preferred form of administration, the stability of the compounds and standard pharmaceutical practice. However, ointments prepared by mixing pranoprofen with the ointment bases such as vaseline, hydrophilic ointment base, absorptive ointment base and so on, which are usually used, exhibit insufficient pharmacological effects as shown in the following pharmacological experiment 1.

As a result of various investigations, the present inventors have found that gelled ointments prepared by mixing (a) 0.5–5% by weight of pranoprofen as an active ingredient with ointment bases comprising (b) 10–90% by weight of at least one member selected from the group consisting of a mono-, bi- or tri-hydric lower aliphatic alcohol, polyethylene glycol having an average molecular weight in the range of 200–1000, methyl ethyl ketone and acetone, (c) 0.1–5% by weight of a gelling agent selected from the group consisting of carboxyvinyl polymer, hydroxyethyl cellulose, alginic acid and carboxymethyl cellulose, (d) an adequate amount, which is sufficient to neutralize the ointments of the present invention, of a water-soluble basic substance selected from the group consisting of ammonia, sodium hydroxide, potassium hydroxide, triethanolamine, diethanolamine, diisopropanolamine, triisopropanolamine and triethylamine, and (e) 10–90% by weight of water is more significantly excellent than the indomethacin ointments used clinically in the pharmaceutical effects and physical properties as ointments.

The mono-, bi- or tri-hydric lower aliphatic alcohol includes commonly used one in the field of pharmaceutical practices such as, preferably, ethanol, isopropanol, propylene glycol or glycerol.

The preferable gelling agent is carboxyvinyl polymer. The amount of the gelling agent may vary depending on the molecular weight, but it is generally in the range of 0.1–5% by weight, preferably 0.5–2% by weight.

The preferable water-soluble basic substance is ammonia, potassium hydroxide, triethanolamine, diethanolamine, diisopropanolamine or triisopropanolamine. The water-soluble basic substance should be added sufficient amount to dissolve pranoprofen in the ointment base and to adjust the pH of the ointment base to 5–9, preferably 6–8. Water is purified water, preferably.

The effects of pranoprofen can be sufficiently expected by adding 0.5–5% by weight, especially 1–3% by weight to the whole weight.

A percutaneous absorption enhancer such as isopropyl myristate, diisopropyl adipate, diethyl sebacate or ester of sebacic acid with propylene glycol, a stabilizer such as dibutylhydroxytoluene, a surfactant, a perfume or a preservative may be added, if desired. Further, a local skin irritant such a nonylic acid vanillylamide may be added.

The ointments of the present invention can be prepared by dissolving pranoprofen in at least one member selected from the group consisting of the mono-, bi- or tri-hydric lower aliphatic alcohol, polyethylene glycol having an average melecular weight in the range of 200–1000, methyl ethyl ketone and acetone, a part of water and the water-soluble basic substance and then mixing the solution with the gelling agent previously swelled in the remaining water, but the order of mixing may be partly modified.

The present invention will be better understood from the following pharmacological experiments and formulation examples, but they are not to be construed as limiting the present invention.

PHARMACOLOGICAL EXPERIMENT 1

Antiinflammatory action on rat carrageenin edema

Male Donryu rats weighing about 150 g, provided by Clea Japan Inc., were divided into groups of 6–14 animals each. After the foot volume of rat hind paw was measured by the water displacement method, the test ointment cantaining pranoprofen prepared in Formulation Example 2 was uniformly applied from the ankle of the hind paw to the tip of the toe (100 mg/paw). The ointment base was also applied to the control group.

The applied region was covered with a thin film (PARAFILM, Amarican Can Co.) to prevent being licked by rat and subjected to the occulative dressing technique (ODT). After 2 hours, PARAFILM was removed and the ointment was wiped off with a gauze immersed in warm water. To induce the edema, a 0.5% methyl cellulose solution (5 ml/200 g) was administered orally and then immediately 0.05 ml of a 1% carrageenin (PICNIN A, Zushikagaku Laboratory, Inc.) in physiological saline was injected subcutaneously into the treated hind paw. Three hours after the injection of carrageenin, the foot volume was measured to calculate the edema rate (%). The inhibitory rate (%) was determined as compared with the control group. The results are statistically analyzed by the one-way layout method.

From the results shown in Table 1, the ointment of the present invention is more potent than the ointment of pranoprofen mixed with ointment bases usually used.

TABLE 1

| Ointment base | Amount of pranoprofen (%) | Number of rats used | Edema rate (%) (mean ± standard error) | Inhibitory rate (%) |
|---|---|---|---|---|
| The ointment of the invention (Formulation example 2) | 0 | 14 | 65.0 ± 3.2 | 43.6 |
|  | 1 | 14 | 36.6 ± 3.1** |  |
| Vaseline | 0 | 6 | 64.6 ± 1.9 | 21.1 |
|  | 1 | 6 | 51.0 ± 7.7 |  |
| Hydrophilic ointment base | 0 | 6 | 51.3 ± 5.6 | 24.6 |
|  | 1 | 6 | 38.7 ± 7.1 |  |
| Polyethylene (5%) Liquid paraffin (95%) | 0 | 6 | 57.6 ± 6.9 | 17.7 |
|  | 1 | 6 | 47.4 ± 6.5 |  |
| Polyethylene (4.75%) Liquid paraffin (90.25%) | 0 | 6 | 48.6 ± 3.3 | 23.4 |
| Ester of fatty acid with glycerol (5%) | 1 | 6 | 37.2 ± 4.1 |  |

**$p < 0.01$ significant vs. control group

PHARMACOLOGICAL EXPERIMENT 2

Comparison with clinically used indomethacin ointment against carrageenin-induced foot edema The experiment was carried out in the similar manner as Experiment 1 except that the inhibitory rate (%) was determined as compared with sham group treated with PARAFILM.

From the results shown in Table 2, the ointment of the present invention is significantly potent in comparison with the indomethacin ointment.

TABLE 2

| Ointment | Amount of pranoprofen (%) | Number of rats used | Edema rate (%) (mean ± standard error) | Inhibitory rate (%) |
|---|---|---|---|---|
| Ointment of the invention | 1 | 14 | 36.6 ± 3.1 | 44.2**+ |
| Sham group | 0 | 14 | 65.6 ± 4.1 |  |
| Indomethacin ointment | 1 | 14 | 46.9 ± 1.3 | 28.5** |

**$P < 0.01$ significant vs. Sham group
+$P < 0.05$ significant vs. indomethacin ointment

PHARMACOLOGICAL EXPERIMENT 3

Action on rat fracture edema

Male Donryu rats weighing about 130 g were divided into groups of 6 animals each. The test ointment was applied uniformly from the ankle of the hind leg to the tip of the toe (100 mg/paw). Then, the applied region was covered with PARAFILM and subjected to ODT. After 2 hours, the PARAFILM was removed and the ointment was wiped off with a gauze immersed in warm water. Then, a 0.5% methyl cellulose solution (5 ml/200 g) was administered orally, and immediately the hind leg of the rat was transversely fractured by being pinched with forceps. Three hours after the fracture, the foot volume was measured by the water displacement method. The rate of increase against the foot volume before the fracture was calculated, and the inhibitory rate (%) was determined as compared with the control group.

The inhibitory rate of the 1% pranoprofen gelled ointment of the present invention is 38%, whereas the rate of the indomethacin ointment is 31%.

PHARMACOLOGICAL EXPERIMENT 4

Action on rat increased vascular permeability induced by carrageenin

Male Donryu rats weighing about 130 g were divided into groups of 7-8 animals each. The backs of the rats were shaved with an electric clipper and an electric shaver, and after 24 hours, 0.1 ml of 1% carrageenin in physiological saline was injected into the dorsal skin. Immediately after the injection, 50 mg of the test ointment was applied. After 2.5 hours 1% Evans blue solution in physiological saline (0.5 ml/100 g) was administered intravenously. After 30 minutes, the rat was bled to death and the dorsal skin was stripped off. The region of the skin dyed blue was cut out and the amount of dye which had leaked (μg/site) was determined by extracting the dye. The results are shown as an inhibitory rate in comparison with the control group.

In addition, to examine the duration of action, carrageenin was injected 24 hours after the test ointment was applied to another group and the same experiment was carried out. In this experiment, the test ointment was removed at the 6th hour.

From the results summarized in Table 3, the 1% pranoprofen gelled ointment of the present invention exerts the same degree of inhibitory action as did the indomethacin ointment, and when carrageenin was given intradermally 24 hours after the application of the test ointment, the gelled ointment of the present invention inhibited significantly increased vascular permeability, while the 1% indomethacin ointement did not show the significant inhibitory action.

TABLE 3

| Ointment | Dose 50 mg/site | Vascular permeability inhibition (%) | |
|---|---|---|---|
|  |  | 3 hr. | 24 + 3 hr. |
| The ointment of the present invention (Formulation Example 11) | 1.0% | 62** | 31* |
| Indomethacin ointment | 1.0% | 61** | 24 |

*$P < 0.05$ significant vs. control group
**$P < 0.01$ significant vs. control group Test ointment was applied topically just before intradermal injection of carrageenin. Effects were measured 3 hours after the injection.

PHARMACOLOGICAL EXPERIMENT 5

Therapeutic effects on rat adjuvant arthritis

Male Lewis rats weighing 280-310 g were divided into groups of 8 animals each. The adjuvant was dead tubercle bacilli suspended in liquid paraffin (0.5 mg/0.1 ml). It was inoculated into the skin at the base of tail. Animals with arthritis were chosen on the 15th day, and the test ointment was applied to the site of the swelling on the right hind leg, 100 mg once a day for 7 consecutive days starting on the 15th day. It was removed at the 6th hour. The foot volume was measured by the water displacement method before the injection of adjuvant, just before the application of ointment on the 15th day, on the 3rd day after the first application (the 18th day) and on the 7th day (on the 22nd day).

The inhibitory rate was determined in comparison with the control group. The inhibitory rate of the 1% pranoprofen gelled ointment of the present invention is 52%, whereas the rate of the 1% indomethacin ointment is 47%.

PHARMACOLOGICAL EXPERIMENT 6

Action on prostaglandin $E_2$ ($PGE_2$) production in rat carrageenin air pouch

Male Donryu rats weighing about 130 g were divided into groups of 6 animals each. The backs of the rats were shaved with an electric clipper and an electric shaver, and then an air pouch of 5 ml was made subcutaneously. After 24 hours, 8 ml of a 1% carrageenin solution in physiological saline was injected into the pouch. A given quantity of the ointment to be tested was immediately applied to the pouch surface, and the liquid in the pouch was recovered after 3 hours. From this solution, substances like $PGE_2$ were extracted, bioassayed using a section of the gastric fundus, and the amount of $PGE_2$-like substances was found by comparison with a standard preparation. Pranoprofen gelled ointment of the present invention inhibited the production of $PGE_2$ in carrageenin air pouches in a concentration-dependent way at 1–3%, showing stronger inhibition than the 1% indomethacin ointment. The 1% pranoprofen gelled ointment inhibited the production of $PEG_2$ in carrageenin air pouches in a dose-dependent way when 50–200 mg was applied, showing stronger activity than the 1% indomethacin ointment.

PHARMACOLOGICAL EXPERIMENT 7

Action on bradykinin-induced nervous-discharge acceleration in cats

Cats weighing 2–3 kg were used regardless of sex. Under mixed anesthesia of laughing gas and halothane, the animals were fixed to a brain-orientation-fixing apparatus, then cut at the $L_1$ or $L_2$ level, and a spinal specimen was prepared. Next, a polyethylene canula for the arterial injection of bradykinin (BK) was inserted into a side branch of the femoral artery of the right hind leg and a similar canula for the intravenous injection of galamine into the median cephalic vein of the left foreleg.

After the completion of the operation, the animal was immobilized with galamine, and the experiment was made with artificial respiration without anesthesia. From the dipole electrode fitted to the saphenous nerve, the action potential of pain nerve was induced, and the action of the test ointment was examined, taking as an index the acceleration of nervous discharge frequency 10–40 seconds after the arterial injection of BK (20 g/0.2 ml). The test ointment (1.5 g) was applied to the skin of the right hind leg, and measurement was periodically made.

The 3% pranoprofen gel strongly inhibited the acceleration of nervous discharge after the arterial administration of BK, starting 90 minutes after its application.

PHARMACOLOGICAL EXPERIMENT 8

Percutaneous absorption and excretion

Male Donryu rats weighing 120–140 g were divided into groups of 4 animals each. The backs of the rats were shaved with an electric clipper and an electric shaver. On the exposed part, aluminum foil (3×4 cm) to which 1% $^{14}C$-pranoprofen gelled ointment (60 mg) had been applied was placed, sealed hermetically with an adhesive plaster, and then massaged from the above for about 1 minute.

After this application, the test ointment remaining was wiped off at a set time with absorbent cotton moistened with 50% ethanol. The contained $^{14}C$ was eluted with methanol and determined by conventional methods.

An adhesive plaster a little larger (3×4 cm) than the application area (2×3 cm) was applied after 24 hours.

After applying 60 mg of the 1% $^{14}C$-pranoprofen gelled ointment, the blood level rapidly rose and nearly reached a plateau (about 1.5 g/ml) in about 3 hours. After removing the unabsorbed ointment (6 hours after application) the blood level rapidly fell at the half-life of about 5 hours.

Pranoprofen gelled ointment is absorbed rapidly by rat skin, with the absorption rate up to the sixth hour after application estimated to be 28.3–33%.

Absorbed pranoprofen disappears from blood at the half life of about 5 hours. It is excreted mainly into urine and feces.

The results of pharmacological experiments suggest that pranoprofen gelled ointment of the present invention rapidly permeates into the site of inflammation after topical application, inhibits the production of prostaglandin $E_2$ at that site, and has strong antiinflammatory and analgesic activities by antagonizing the pain-inducing effect of bradykinin. Moreover, pranoprofen gelled ointment is believed to have the characteristic of excellent penetration into deep regions with inflammation such as joints, and to have long-sustained action. These activities of pranoprofen gelled ointment are superior to those of indomethacin ointment and its safety is also greater. In conclusion, pranoprofen gelled ointment of the present invention is expected to be clinically useful.

FORMULATION EXAMPLE 1

To 52 g of ethanol are added 1 g of pranoprofen and 2 g of triisopropanolamine. To the mixture are added 30 g of a 5% carboxyvinyl polymer solution (HIVIS-WAKO 104, Wako Pure Chemical Industries, Ltd.) and 15 g of purified water.

The pH of ointment thus obtained is 6.6 and the viscosity, which is measured at 20° C. and 20 rpm by using a BH type viscometer (Tokyo Keiki Seisakusho KK.) provided with Roter No. 7, is 460 poises.

This ointment is transparent, spreads well on the skin, gives an impression of refreshment, and is stable when kept at room temperature.

FORMULATION EXAMPLE 2

A solution of 1 g of pranoprofen in a mixture of 2 g of diisopropanolamine, 8 g of propylene glycol, 2 g of diisopropyl adipate and 37 g of ethanol is mixed with a solution of 2 g of carboxyvinyl polymer (CARBOPOL 934, Goodrich Chemical Co.) in 48 g of purified water to give an ointment with a pH of 6.4 and a viscosity of 980 poises.

FORMULATION EXAMPLE 3

A solution of 1 g of pranoprofen in 14 g of 2N potassium hydroxide is mixed with 30 g of a 5% HIVIS-WAKO 104 solution, and then with 12 g of ethanol and 43 g of purified water to give an ointment with a pH of 8.0 and a viscosity of 670 poises.

FORMULATION EXAMPLE 4

A solution of 3 g of pranoprofen and 5 g of triisopropanolamine in a mixture of polyethylene glycol 400 and 32 g of ethanol is mixed with 40 g of a 4% HIVISWAKO 104 solution to give an ointment with a pH of 7.2 and a viscosity of 250 poises.

FORMULATION EXAMPLE 5

A solution of 3 g of pranoprofen and 5 g of triisopropanolamine in a mixture of 20 g of glycerol and 32 g of ethanol is mixed with 30 g of a 5% HIVISWAKO 104 solution and 0.1 g of dibutylhydroxytoluene. To the mixture is added purified water to make the whole quantity of 100 g.

The pH of the ointment thus obtained is 6.7 and the viscosity is 610 poises.

FORMULATION EXAMPLE 6

A solution of 2 g of pranoprofen and 4 g of triisopropanolamine in 34 g of acetone is mixed with 20 g of a 5% HIVISWAKO 104 solution to give ointment with a pH of 7.3 and a viscosity of 310 poises.

FORMULATION EXAMPLE 7

A solution of 0.5 g of pranoprofen and 2 g of triethanolamine in a mixture of 20 g of methyl ethyl ketone and 17.5 g of ethanol is mixed with a 5% HIVISWAKO 104 solution and 40 g of purified water to give an ointment with a pH of 7.3 and a viscosity of 220 poises.

FORMULATION EXAMPLE 8

To a solution of 1 g of pranoprofen in 10 g of a 5% ammonia solution are added 40 g of purified water and 20 g of isopropanol. The solution is mixed with 20 g of a 5% CARBOPOL 934 solution to give an ointment with a pH of 8.7 and a viscosity of 164 poises.

FORMULATION EXAMPLE 9

A solution of 0.5 g of pranoprofen and 1.5 g of diethanolamine in 46 g of ethanol and 30 g of propylene glycol is mixed with a gelling agent comprising 1 g of HIVISWAKO 104 and 1 g of hydroxyethyl cellulose in 20 g of purified water to give an ointment with a pH of 6.7 and a viscosity of 360 poises.

FORMULATION EXAMPLE 10

A solution of 0.5 g of pranoprofen and 2 g of diisopropanolamine in 20 g of ethanol is mixed with a mixture of 2 g of HIVISWAKO 104 in 10 g of purified water and 40 g of glycerol.

To the mixture is added glycerol to make the whole quantity to 100 g. The pH of the ointment is 6.8 and the viscosity is 580 poises.

FORMULATION EXAMPLE 11

A solution of 1 g of HIVISWAKO 104 in a mixture of 56.5 g of purified water and 30 g of ethanol is mixed with 5 g of propylene glycol and 2 g of diethyl sebacate. After 1 g of pranoprofen is suspended in the mixture, 3.5 g of triisopropanolamine is added to the suspension and then 1 g of polyethylene glycol 4000 is added to give an ointment with a pH of 7.6 and a viscosity of 400 poises.

What is claimed is:

1. An antiinflammatory and analgesic gelled ointment containing 0.5–5% by weight of pranoprofen, 10–90% by weight of at least one member selected from the group consisting of a mono-, bi- or tri-hydric lower aliphatic alcohol, polyethylene glycol having an average molecular weight in the range of 200–1000, methyl ethyl ketone and acetone, 0.1–5% by weight of a gelling agent selected from the group consisting of carboxyvinyl polymer, hydroxyethyl cellulose, alginic acid and carboxymethyl cellulose, an adequate amount of a water-soluble basic substance selected from the group consisting of ammonia, sodium hydroxide, potassium hydroxide, triethanolamine, diethanolamine, diisopropanolamine, triisopropanolamine and triethylamine, and 10–90% by weight of water.

2. The ointment of claim 1 wherein the mono-, bi- or tri-hydric lower aliphatic alcohol is ethanol, isopropanol, propylene glycol or glycerol.

3. The ointment of claim 1 wherein the gelling agent is carboxyvinyl polymer.

4. The ointment of claim 1 wherein the water-soluble basic substance is ammonia, potassium hydroxide, triethanolamine, diethanolamine, diisopropanolamine or triisopropanolamine.

5. The ointment of claim 1 which further contains a percutaneous absorption enhancer.

6. The ointment of claim 5 wherein the percutaneous absorption enhancer is selected from the group consisting of isopropyl myristate, diisopropyl adipate, diethyl sebacate and ester of subacic acid with propylene glycol.

* * * * *